(12) United States Patent
Lai

(10) Patent No.: US 10,191,544 B2
(45) Date of Patent: Jan. 29, 2019

(54) HAND GESTURE RECOGNITION SYSTEM FOR CONTROLLING ELECTRONICALLY CONTROLLED DEVICES

(71) Applicant: HORSEMOON LLC, San Jose, CA (US)

(72) Inventor: Hing Yin Lai, San Jose, CA (US)

(73) Assignee: Horsemoon LLC, San Jose, CA (US)

( * ) Notice: Subject to any disclaimer, the term of this patent is extended or adjusted under 35 U.S.C. 154(b) by 0 days.

(21) Appl. No.: 15/531,975

(22) PCT Filed: May 6, 2015

(86) PCT No.: PCT/US2015/029560
§ 371 (c)(1),
(2) Date: May 31, 2017

(87) PCT Pub. No.: WO2016/089442
PCT Pub. Date: Jun. 9, 2016

(65) Prior Publication Data
US 2017/0329403 A1 Nov. 16, 2017

Related U.S. Application Data

(60) Provisional application No. 62/088,572, filed on Dec. 6, 2014.

(51) Int. Cl.
*G06F 3/01* (2006.01)
*A61B 5/024* (2006.01)
*G06F 3/0346* (2013.01)

(52) U.S. Cl.
CPC .......... *G06F 3/014* (2013.01); *A61B 5/02438* (2013.01); *G06F 3/017* (2013.01);
(Continued)

(58) Field of Classification Search
CPC ........ G06F 3/014; G06F 3/017; G06F 3/0346; G08C 2201/32; A61B 2562/0219;
(Continued)

(56) References Cited

U.S. PATENT DOCUMENTS

2003/0149803 A1* 8/2003 Wilson ................. G06F 3/0346
710/1
2011/0163947 A1* 7/2011 Shaw .................... G06F 3/0346
345/156
(Continued)

FOREIGN PATENT DOCUMENTS

WO WO2008150809 12/2008

*Primary Examiner* — Dionne H Pendleton
(74) *Attorney, Agent, or Firm* — Craig M. Stainbrook; Stainbrook & Stainbrook, LLP

(57) ABSTRACT

A remote control including a sensing device incorporated into wristband and having sensors to provide signal inputs relating to the pitch, roil and yaw movements of a user's wrist. A continuous feedback loop with a drift detector receives the sensor signal inputs and a rotation matrix input and uses the sensor signal inputs to calculate a numerical error, A proportional-integral controller receives the calculated numerical error output from the drift detector and outputs a control output to a drift adjuster. A gyroscope provides an input to the drift adjuster to correct for instrument drift and to provide an output to conduct a kinematics and normalization calculation and output a rotation matrix. The feedback loop employs upper and Sower bounds for the rotational matrix to eliminate grossly anomalous feedback numerical errors in sensor device inputs due to sudden angle changes in pitch, roll, or yaw.

18 Claims, 4 Drawing Sheets

(52) U.S. Cl.
CPC .... *G06F 3/0346* (2013.01); *A61B 2562/0219* (2013.01); *G08C 2201/32* (2013.01)

(58) Field of Classification Search
CPC ....... A61B 5/02438; H04N 2005/4432; H04N 21/42204
See application file for complete search history.

(56) References Cited

U.S. PATENT DOCUMENTS

| | | |
|---|---|---|
| 2013/0217998 A1 | 8/2013 | Mahfouz et al. |
| 2014/0139432 A1 | 5/2014 | Shaw et al. |
| 2015/0231491 A1* | 8/2015 | Hwang ............... A63F 13/2145 345/161 |
| 2015/0287338 A1* | 10/2015 | Wells ................. G09B 19/0038 702/19 |
| 2016/0062469 A1* | 3/2016 | Abi-Rached ............ G06F 3/017 345/156 |
| 2017/0208251 A1* | 7/2017 | Shamir ..................... G06T 7/33 |
| 2018/0008141 A1* | 1/2018 | Krueger ................ A61B 5/744 |

\* cited by examiner

Othogonality rule: rows and columns are supposed to be perpendicular to each other. However numerical errors could cause them to lean to each other just like this box

HAND GESTURE RECOGNITION SYSTEM FOR CONTROLLING ELECTRONICALLY CONTROLLED DEVICES

BACKGROUND OF THE INVENTION

Technical Field

The invention relates most generally to motion control input devices, and more specifically to a handheld motion control device for controlling the movement of powered devices having electronically controlled motion.

Background Art

Existing handhold motion controllers from Wii®, XBOX® and PLAYSTATION® are known, as are virtual reality input apparatus, including virtual reality gloves, which use multiple sensors to detect line movements of fingers and hands. However, VR input devices must include yaw rotation to simulate the virtual movement of a user's hand or body on a 2 dimensional television screen. As such, they cannot be "repurposed" to control a physical object in three dimensional space. (WII is a registered trademark Nintendo of America, Inc., of Redmond, Wash., XBOX is a registered trademark of Microsoft Corporation of Redmond, Wash.; PLAYSTATION is a registered trademark of Kabushiki Kaisha Sony Computer Entertainment IA Sony Computer Entertainment inc., of Tokyo, japan.)

The popular motion controller from Leap Motion supplements mouse and keyboard input and eliminates the need to physically contact computer input devices, but it requires that a user's hand and finger be in close proximity to the (non wearable) motion tracker so that motions can be detected. It does not enable a user to move around freely to control a physical running object.

In short, known remote controllers on the market and in the published art are controlled by lingers and palm movement. What is needed is a hands free motion controller that requires no finger or palm movement: to control a moving object in three dimensional space (e.g., directions left, right, forward and backward). The present invention provides such a solution.

The foregoing patents reflect the current state of the art of which the present inventor is aware. Reference to, and discussion of, these patent is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

Disclosure of Invention

The present invention is a hand gesture motion control system for remotely controlling a controlled device. In its most essential aspect, the inventive remote control system includes a sensing device incorporated into wristband, such as a watch or bracelet. The sensing device includes sensors that provide sensor signal inputs relating to the pitch, roll and yaw movements of the user's wrist about X, Y, and Z axes, respectively. The system next includes a continuous feedback loop with a drift detector to receive the sensor signal inputs as well as a rotation matrix input and then to use the sensor signal inputs to calculate a numerical error. It also includes: a proportional-integral controller to receive the calculated numerical error output from the drift detector and to output a control output to a drift adjuster; and at least one gyroscope providing an input to the drift adjuster with which to correct for instrument drift and to provide an output to conduct a kinematics and normalization calculation and to output a rotation matrix. The feedback loop employs upper and lower bounds for the rotational matrix to eliminate grossly anomalous feedback numerical errors in sensor device inputs due to sudden angle changes in pitch, roll or yaw.

BRIEF DESCRIPTION OF THE DRAWINGS

The invention will be better understood and objects other than those set forth above will become apparent when consideration is given to the following detailed description thereof. Such description makes reference to the annexed drawings wherein.

BEST MODE FOR CARRYING OUT THE INVENTION

Figure 1:
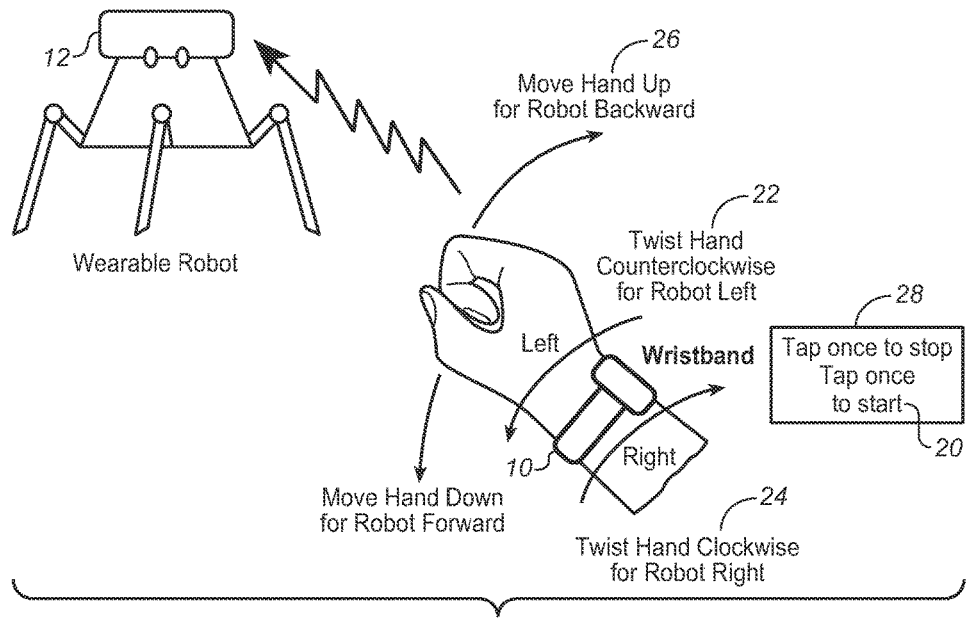
FIG. 1 is a highly schematic view showing the hand gesture recognition device of the present invention incorporated in a wristband or bracelet, along with a device under the control of the hand gesture recognition device.

In its most essential aspect, the hand gesture motion control system or the present invention comprises a sensing device incorporated into and/or embedded inside a bracelet or wristband, such as a wristwatch 10, such as the one schematically illustrated in FIG. 1. (As used herein, the term "wristband" shall be taken to mean a wristband, wristwatch, bracelet, and the like, inclusively.) The motion sensors in the wristband detect user hand rotation (roll and pitch) to control the direction of movement of a physical object, such as a remote controlled car, truck, plane, boat, helicopter, multi-rotor (quadracopter robot, etc., 12, or, alternatively, the environmental conditions of a room or any other physical apparatus amenable to remote control inputs involving changes in inputs from two or three orthogonal sensors.

Figure 2:
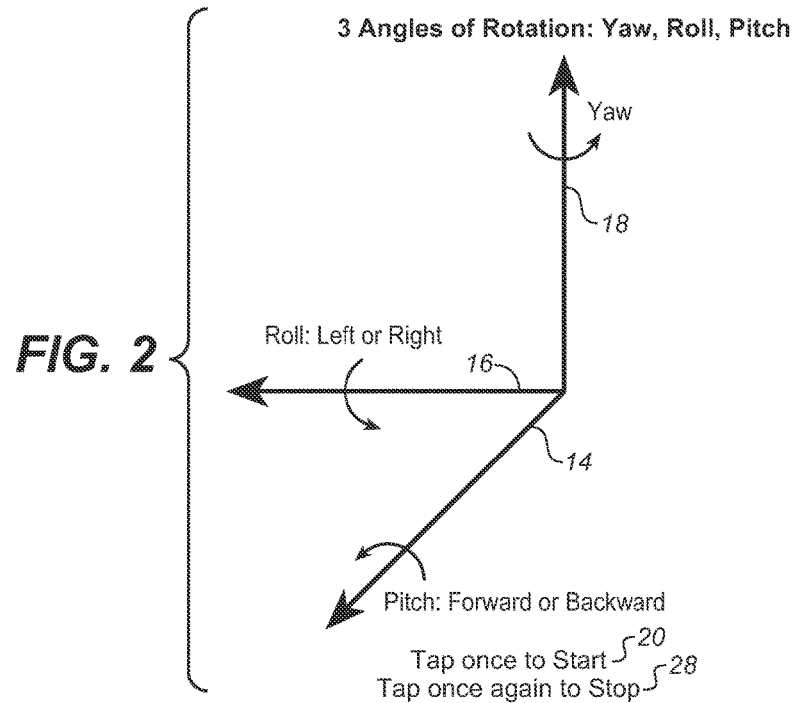
FIG. 2 is a schematic view illustrating the three elements of rotation of the hand gesture recognition device (viz., roll, pitch and yaw), corresponding to and recognized as effected by forearm and hand movements, such as pronation, supination, elevation (e.g., flexion) and depression (e.g., extension)

As seen in FIG. 2, rotation has three elements (pitch 14, roll 16, and yaw 18). Yaw rotation follows a user's body turn movement or any independent motion of the hand and arm that changes the cardinal direction (compass heading) of the controller. Without using yaw rotation, the bracelet enables a user to move, run, and turn freely to follow and control a physically moving object using only hand gestures.

Referring again to FIG. 1 the hand gesture recognition device is embedded inside a wristband or bracelet for following several applications. For a robotic control (car, helicopter, quadrone): tapping the controller once turns on the controller (power on 20; left turns involve twisting the hand counterclockwise (pronation) 20; right turns entail twisting the hand (supination) clockwise 22; forward motion entails moving the hand down 24; backward motion entails moving the hand up 26; and tapping the controller once powers the controller on, and tapping it again, once, thereafter turns it off 28. It is turned on again with another single tap.

Room environmental controls are functionally comparable. Light brightness/dimness and temperature increases and decreases can be mapped to correspond to the gesture recognition program. For instance, increasing room light and dimming light may involve supination pronation, respectively; temperature increases and decreases may be similarly programmed or may involve elevation and depression, respectively, of the wrist.

Referring next to FIG. 2, it is again seen that there are three angles of rotation in three dimensional axes, which include pitch 14, roll 16, and yaw 18. The inventive hand gesture recognition device uses pitch 14 and roll 16 for hand gesture control. Yaw rotation 18 follows both user hand and body turn movement. As such, yaw cannot be controlled by hand movement alone. Yaw can be used for left or right direction control, much as a motion controller from or PLAYSTATION®, because a user's body always laces a visual display in one direction for a virtual game. However, in the physical world to control a physical object, a user will almost always turn his or her entire body while following a moving object. This makes changes in bodily orientation (turns right and left, or clockwise and counterclockwise about the vertical anatomical axis) as a yaw input ill-suited for user control of left and right movement of a physical object in the real world.

Figure 3:
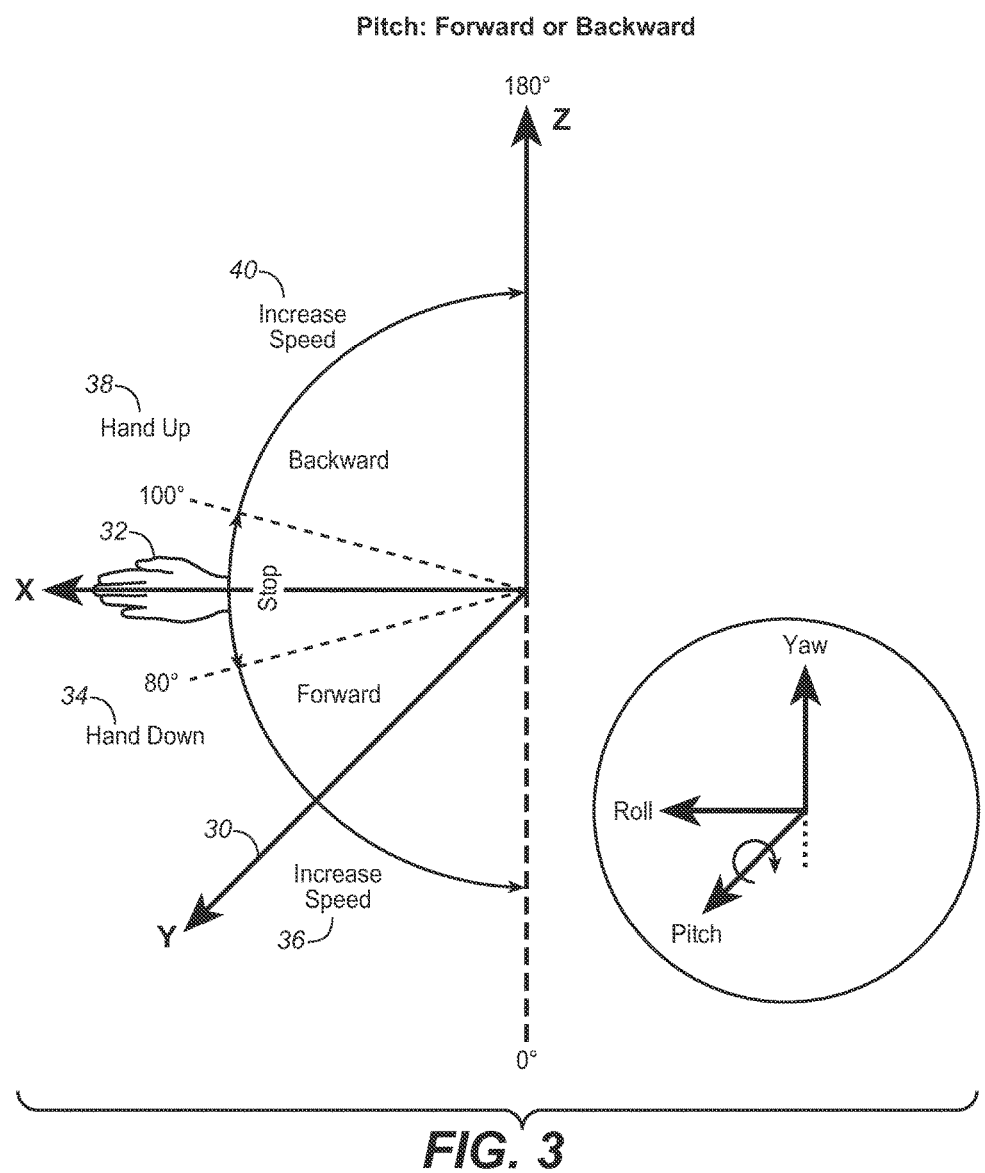
FIG. 3 illustrates a hand gesture involving pitch rotation about a Y axis to control forward and backward direction of the electronically controlled device.

Referring now to FIG. 3, the inventive hand gesture control device uses rotation about a Y axis (pitch) 30 to control the forward and backward direction of the device under control. Moving the hand and wrist up and down is equivalent to rotation about the Y axis.

Held at an initial (substantially level) forearm angle 32 to define an initial generally horizontal plane and to define the idle or stopped condition, lowering the hand and wrist 34 (for example, 80 degrees) from the horizontal (hand down angle) will provide a forward control input. Further decreasing the degree 36 (hand down further from a horizontally oriented axis) translates into increasing forward speed.

A return to the horizontal 32 will return the remotely controlled device to an idle, stopped condition.

Then, elevating the hand and wrist 38, and thus tipping the controller backwardly toward the user, an angle up condition relative to the horizontal (e.g., 100 degrees to 180 degrees) will provide a control input to cause reverse direction of the device under control. Increasing the degree of backward tilt 40 (with the hand and wrist still further elevated from the horizontal) translates into increasing reverse (backward) speed.

Figure 4:
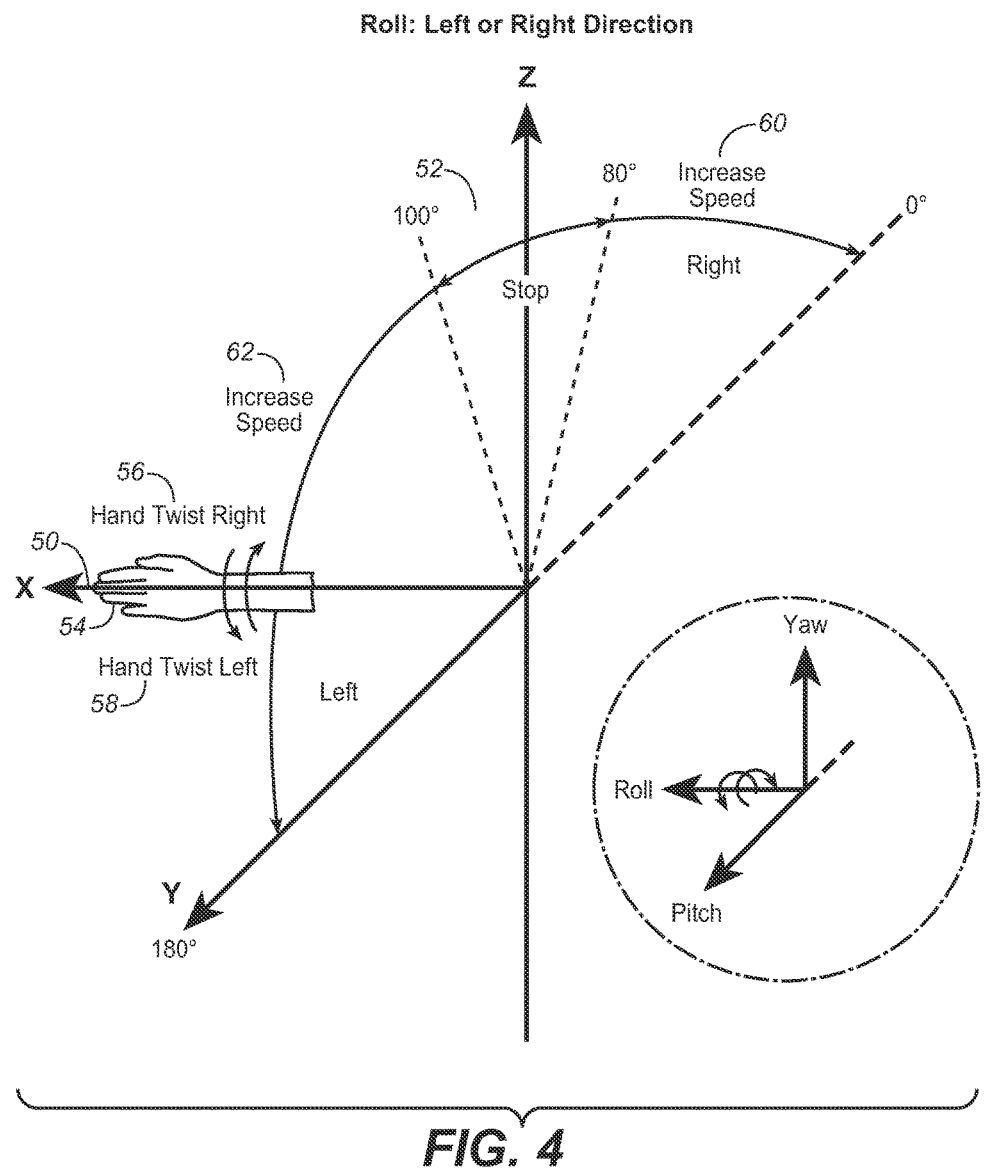
FIG. 4 illustrates the hand gesture control involving roll rotation about an X axis to control left and right direction of the electronic device.

Referring next to FIG. 4, the hand gesture control apparatus of the present invention uses rotation about the X axis 50 to control left and right directional movement of the device under control. An initial idle right/left directional control condition may be established with a palm oriented roughly 80 to 100 degrees from the vertical 52 (the corresponding hand orientation shown at 54). Then, twisting the hand clockwise 56 or counterclockwise 58 is equivalent to rotation about the X axis. Using an initial "roll" position, twisting the hand clockwise effects a right turn input. Decreasing the degree 60 (twisting the hand further clockwise, thus further from the initial idle orientation) causes an increase in right turn speed input. Conversely, counterclockwise rotation 58 about the X axis causes a left turn control input, and further counterclockwise rotation 62 increases the left turn speed.

Figure 5:
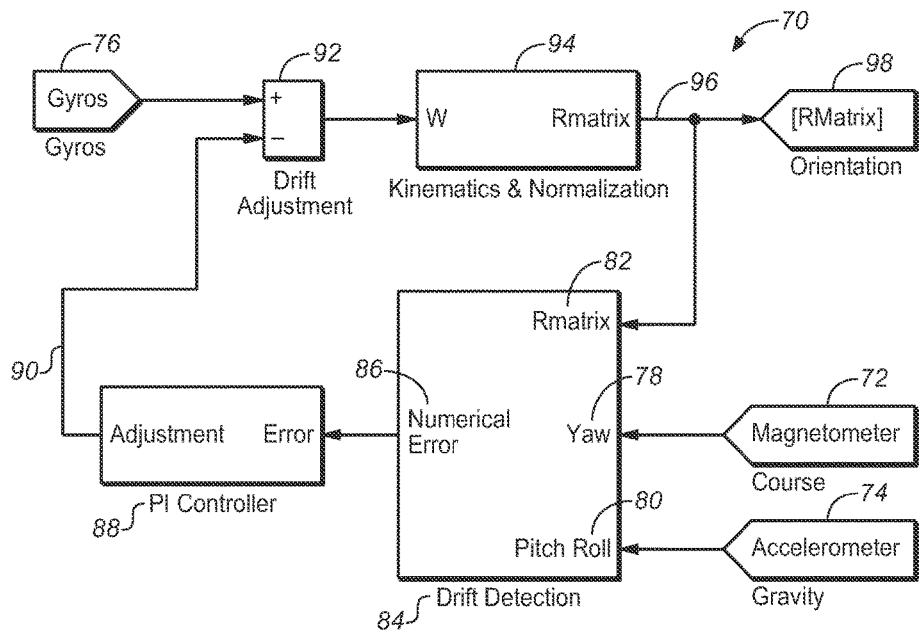
FIG. 5 is a highly schematic block diagram illustrating the input from various motion sensors and means for correcting for feedback numerical errors in the system motion algorithm.
Figure 5:
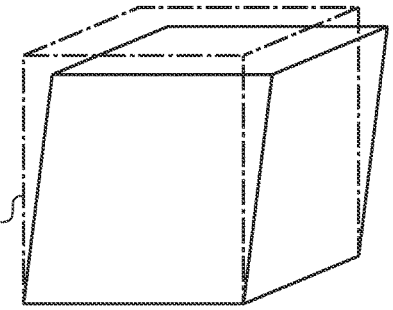

Referring next to FIG. 5, a further improvement provided by the present invention stems from the use of upper and lower bounds for feedback numerical errors in the motion control algorithm. The motion control algorithm executed by the system microcontroller is written for airplane control and is modified to prohibit gross anomalies (sudden angle changes) in pitch, roll, and yaw inputs within each time step. In real world control conditions, hand movements can be very fast and sudden—In all directions within each time step. Such sudden movements will twist the orthogonal dimension and generate a large magnitude in feedback numerical error. Accordingly, the present invention applies an algorithm that: adjusts for any unrealistically large numerical errors by having the rotation matrix algorithm no longer generates correct pitch, roll, and yaw angles within each time step. With upper bound and lower bounds, numerical errors are capped to stabilize the continuous feedback loop condition 70.

Initial course, tilt, orientation, and inclination conditions at power on are established using sensors such as a magnetometer 72, accelerometer 74, and one or more gyroscopes 76 (preferably MEMS gyroscopes). Yaw sensor input 78 from the magnetometer, and pitch and roll sensor input 80 from the accelerometer, are detected and analyzed, along with a rotational matrix input signal 82 (described more fully below), by a drift detection algorithm 84 that outputs a numerical error 86 to a proportional-integral controller 88. At every sampling cycle the proportional integral controller takes the numerical error (drift detection) output and uses an established PI algorithm to calculate an error value according to upper and lower limit setpoints imposed on the controller. The controller output 90 is an input used for instrument drift adjustment 92 (for instance, for bias and sensitivity drill varying according to temperature), the drift adjustment also using as an input the signal or signals of the gyroscope(s), which can detect even small movements of the hand gesture motion control device about any of the three X, Y, and Z axes. The controller output signal and gyroscope signal(s) then pass to a kinematics and normalization algorithm 94 to describe the controlled device motion. The output is a rotational matrix 96 with probability distributions brought into alignment under an orthogonality rule according to upper and lower matrix limits imposed on the algorithm. The rotational matrix signal is returned to the continuous feedback loop and is also used as the device orientation to control the output signal to the controlled device 98 for smooth and continuous operation of the controlled device within device-specific acceptable control parameters. Under the orthogonality rule 100, the continuous loop feedback algorithm uses upper and lower hounds for the rotational matrix to eliminate grossly anomalous numerical errors such that errors in one row or column of the matrix do not unduly and adversely affect other expressions in the matrix.

The foregoing disclosure is sufficient to enable those with skill in the relevant art to practice the invention without undue experimentation. The disclosure further provides the best mode of practicing the invention now contemplated by the inventor.

While the particular apparatus and method herein shown and disclosed in detail is fully capable of attaining the objects and providing the advantages stated herein, it is to be understood that it is merely illustrative of the presently preferred embodiment of the invention and that no limitations are intended to the detail of construction or design herein shown other than as defined in the appended claims. Accordingly, the proper scope of the present invention should be determined only by the broadest interpretation of the appended claims so as to encompass all such modifications as well as all relationships equivalent to those illustrated in the drawings and described in the specification.

What is claimed as invention is:

1. A hand gesture motion control system for remotely controlling a controlled device, comprising:
   a sensing device incorporated into wristband, said sensing device including sensors providing sensor signal inputs relating to the pitch and roll and yaw movements of the user's wrist about X, Y, and Z axes, respectively; and
   a continuous feedback loop having a drift detector to receive the sensor signal inputs as well as a rotation matrix input and to use the inputs to calculate a numerical error, a proportional-integral controller to receive the calculated numerical error output from said drift detector and to output a control output to a drift adjuster, and at least one gyroscope providing an input to said drift adjuster with which to correct for instrument drift and to provide an output to conduct a kinematics and normalization calculation and to output a rotation matrix;
   wherein said continuous feedback loop employs upper and lower bounds for the rotational matrix to eliminate grossly anomalous feedback numerical errors inputs to said sensing device due to sudden angle changes in pitch, roll, or yaw.

2. The hand gesture motion control system of claim 1, wherein said sensors include at least one accelerometer.

3. The hand gesture motion control system of claim 2, wherein said sensors include at least one accelerometer and one magnetometer.

4. The hand gesture motion control system of claim 3, further including at least one gyroscope.

5. The hand gesture motion control system of claim 4, wherein said magnetometer provides yaw signals and said at least one accelerometer provides pitch and roll signals.

6. The hand gesture motion control system of claim 1, wherein said kinematics and normalization algorithm describes the object motion and outputs a rotational matrix that brings probability distributions into alignment under an orthogonality rule according to upper and lower bounds imposed on the algorithm.

7. The hand gesture motion control system of claim 1, wherein said rotation matrix is passed back into said continuous feedback loop and is also output as a calculated orientation of said sensing device for use in controlling the controlled device.

8. The hand gesture motion control system of claim 7, wherein large numerical errors in one row or column of the matrix do not adversely affect other expressions in the matrix.

9. The hand gesture motion control system of claim 1, wherein the controlled device is a selected from the group consisting of remote controlled car, truck, plane, boat, helicopter, or multirotor, and robot.

10. The hand gesture motion control system of claim 1, wherein the controlled device is a room for human habitation, including its lighting and temperature conditions.

11. The hand gesture motion control system of claim 1, wherein yaw rotation follows a user's body turn movement as well as independent motions of the hand and arm that change the cardinal direction (compass heading) of said sensor device.

12. The hand gesture motion control system of claim 1, wherein said system is powered on with a single finger tap.

13. The hand gesture motion control system of claim 1, wherein counterclockwise rotation of the wrist causes the system to generate and send a signal to a controlled device to make a left turn, and clockwise rotation of the wrist causes said system to generate and send a signal to the controlled device to make a right turn.

14. The hand gesture motion control system of claim 1, wherein moving the hand down causes said system to generate and transmit a signal to the controlled device to move forward and moving the hand down causes said system to generate and send a signal to the controlled device to move backward.

15. The hand gesture motion control system of claim 1, wherein rotation about a Y axis controls the forward and backward direction of the device under control, and wherein moving the hand and wrist up and down is equivalent to rotation about the Y axis.

16. The hand gesture motion control system of claim 15, wherein increasing displacement of the user's hand from an initial idle position increases the forward or reverse direction of the device under control.

17. The hand gesture motion control system of claim 1, wherein rotation about a X axis controls left and right directional movement of the device under control, and rotation of the wrist in a clockwise or counterclockwise is equivalent to rotation about the X axis.

18. The hand gesture control system of claim 17, wherein increasing rotation about the X axis increases the angular displacement from an initial non-turning condition of the device under control and increases the sharpness of the right or left turn made by the device under control.

* * * * *